(12) United States Patent
Zelina et al.

(10) Patent No.: US 7,186,374 B2
(45) Date of Patent: *Mar. 6, 2007

(54) VAPOR PHASE DECONTAMINATION OF CONTAINERS

(75) Inventors: Francis J. Zelina, Lake City, PA (US); Gerald E. McDonnell, Chardon, OH (US); Aaron L. Hill, Erie, PA (US); Thaddeus Mielnik, Concord, OH (US); Iain F. McVey, Lakewood, OH (US); Peter J. Buczynski, Girard, PA (US)

(73) Assignee: Steris Inc., Temecula, CA (US)

( * ) Notice: Subject to any disclaimer, the term of this patent is extended or adjusted under 35 U.S.C. 154(b) by 882 days.

This patent is subject to a terminal disclaimer.

(21) Appl. No.: 10/077,224

(22) Filed: Feb. 15, 2002

(65) Prior Publication Data

US 2002/0159915 A1 Oct. 31, 2002

Related U.S. Application Data (60) Provisional application No. 60/269,659, filed on Feb. 16, 2001, provisional application No. 60/269,549, filed on Feb. 16, 2001.

(51) Int. Cl.
*A61L 9/00* (2006.01)

(52) U.S. Cl. .............................. 422/28; 422/1; 422/29; 422/293; 422/302; 422/305

(58) Field of Classification Search ................. 422/28, 422/1, 29, 292, 293, 302, 305
See application file for complete search history.

(56) References Cited

U.S. PATENT DOCUMENTS

| | | | | |
|---|---|---|---|---|
| 2,175,682 A | * | 10/1939 | Chaffee | 141/85 |
| 3,486,840 A | * | 12/1969 | Burton et al. | 422/26 |
| 3,531,908 A | * | 10/1970 | Rausing et al. | 53/426 |
| 4,169,123 A | | 9/1979 | Moore et al. | |
| 4,909,999 A | * | 3/1990 | Cummings et al. | 422/298 |
| 4,973,449 A | | 11/1990 | Kolstad et al. | |
| 4,992,247 A | | 2/1991 | Foti | 422/304 |
| 5,007,232 A | | 4/1991 | Caudill | |
| 5,145,642 A | | 9/1992 | Feathers, III et al. | |
| 5,173,259 A | | 12/1992 | Bordini | |
| 5,178,841 A | | 1/1993 | Vokins et al. | |
| 5,258,162 A | | 11/1993 | Andersson et al. | |
| 5,313,990 A | * | 5/1994 | Clusserath | 141/6 |
| 5,445,792 A | * | 8/1995 | Rickloff et al. | 422/28 |
| 5,564,481 A | * | 10/1996 | Clusserath | 141/92 |
| 5,600,142 A | | 2/1997 | Van Den Berg et al. | |

(Continued)

FOREIGN PATENT DOCUMENTS

DE 4305478 8/1994

(Continued)

*Primary Examiner*—Krisanne Jastrzab
(74) *Attorney, Agent, or Firm*—Fay, Sharpe, LLP (57) ABSTRACT

A flash vapor generator (10) provides a constant flow of vaporized hydrogen peroxide for rapidly sterilizing a large decontamination tunnel (11) with a high container throughput. The vaporizer includes a heated block which defines an interior bore or bores. The conditions within the decontamination tunnel are carefully monitored to avoid condensation of the vapor while maintaining the vapor as close as possible to the saturation limit.

30 Claims, 8 Drawing Sheets

U.S. PATENT DOCUMENTS

| | | |
|---|---|---|
| 5,634,880 A | 6/1997 | Feldman et al. |
| 5,673,535 A * | 10/1997 | Jagger .................. 53/282 |
| 5,720,148 A * | 2/1998 | Bedin et al. ............ 53/167 |
| 5,733,503 A | 3/1998 | Kowatsch et al. |
| 5,779,973 A | 7/1998 | Edwards et al. |
| 5,788,925 A | 8/1998 | Pai et al. |
| 5,792,435 A | 8/1998 | Mueller et al. |
| 5,837,193 A | 11/1998 | Childers et al. |
| 5,848,515 A | 12/1998 | Catelli et al. |
| 5,872,359 A | 2/1999 | Stewart et al. |
| 5,876,664 A * | 3/1999 | Childers et al. ........ 422/28 |
| 5,879,648 A | 3/1999 | Hada et al. ............ 422/304 |
| 5,949,958 A * | 9/1999 | Naperkowski et al. .... 392/399 |
| 6,077,480 A * | 6/2000 | Edwards et al. ......... 422/28 |
| 6,094,523 A | 7/2000 | Zelina et al. |
| 6,120,730 A | 9/2000 | Palaniappan et al. ..... 422/28 |
| 6,345,452 B1 * | 2/2002 | Feuilloley et al. ...... 34/437 |
| 6,702,985 B1 * | 3/2004 | Taggart et al. ......... 422/28 |
| 2002/0122838 A1 * | 9/2002 | Anderson et al. ........ 425/149 |

FOREIGN PATENT DOCUMENTS

| | | |
|---|---|---|
| EP | 0774263 A1 | 11/1996 |
| FR | 2774912 | 8/1999 |

* cited by examiner

VAPOR PHASE DECONTAMINATION OF CONTAINERS

This application claims the priority of U.S. Provisional Application Ser. No. 60/269,549, filed Feb. 16, 2001, and U.S. Application Ser. No. 60/269,659, filed Feb. 16, 2001.

BACKGROUND OF THE INVENTION

The present invention relates to the sterilization arts. It finds particular application in conjunction with hydrogen peroxide vaporization systems for the sterilization of packaging containers, and will be described with particular reference thereto. It should be appreciated, however, that the invention is also applicable to other chemical vaporization systems such as peracetic acid vaporization systems.

Packaging plants, which use filling lines for filling containers with beverages, food, pharmaceuticals, and the like, are moving to aseptic processing techniques to ensure that the finished product is free of hazardous microorganisms and to maintain the shelf life of the product. As a part of the aseptic process, the containers are microbially decontaminated prior to filling. Bottles or other containers are typically decontaminated using liquid chemical antimicrobial agents, including liquid hydrogen peroxide and peracetic acid, often at elevated temperatures. An alternative approach is to blow mold the containers immediately prior to filling (known, as a blow, fill, and seal process). The concept assumes that the heat involved in the molding process will render the materials used to form the containers sterile.

Recently, hydrogen peroxide vapor has been used as a sterilant. In one method, liquid hydrogen peroxide is sprayed onto the containers. The containers are heated to convert the liquid to a vapor. In another, method hydrogen peroxide vapor is condensed on the surface of the containers to form a thin layer of liquid hydrogen peroxide. In both liquid and vapor hydrogen peroxide sterilization processes, UV radiation has been used with a view to promoting sterilization. Vaporized hydrogen peroxide is a particularly useful sterilant for these purposes because it is effective at low temperatures. Keeping the temperature of the enclosure near room temperature eliminates the potential for thermal degradation of associated equipment and items to be sterilized within the enclosure. In addition, hydrogen peroxide readily decomposes to water and oxygen, which, of course, are not harmful to the operator.

Outside of the container sterilization field, several different methods have been developed for delivering a vapor phase sterilant to an enclosure for sterilizing a load. In one option, the "deep vacuum" approach, a deep vacuum is used to pull liquid sterilant into a heated vaporizer. Once vaporized, the sterilant is propelled by its vapor pressure into an evacuated and sealed chamber. In another option, the "flow-through" approach, vaporized sterilant is mixed with a flow of carrier gas, such as air, that serves to deliver the sterilant into, through, and out of the chamber, which may be at a slightly negative or positive pressure. A solution of about 35% hydrogen peroxide in water is injected into the vaporizer as fine droplets or mist through injection nozzles. The droplets fall on a heated surface which heats the droplets to form the vapor, without breaking it down to water and oxygen. A heated carrier gas is often used to ensure that the heat transfer surface remains at or above the boiling temperature of the hydrogen peroxide.

Trace amounts of hydrogen peroxide on food packaging can affect the flavor of the product or result in other undesirable changes, such as a change in the color of the product. Food packaging regulations now limit hydrogen peroxide residues on containers to a maximum of 0.5 ppm in the United States. Liquid hydrogen peroxide sterilization and condensed vapor sterilization systems are currently unable to meet these stringent regulations without extensive post sterilization processing. For example, rinsing has been used in an attempt to remove the hydrogen peroxide residues. However, unless a high purity water supply can be assured, which tends to be costly, recontamination of the sterilized containers is likely to occur. Heat, for example a 400° C. drying phase, has also been used to attempt to reduce the residual level, but adds considerably to processing time and cost and cannot generally be used with thin-walled plastic bottles.

Additionally, current vaporization systems are unable to handle the latest, high speed bottling plants. With bottles being processed and filled at rates of up to 1000 bottles per minute, or more, it is desirable to have a sterilization system that can supply sterilized bottles at a sufficient rate to meet this demand. The capacity of current drip-feed vaporizers is limited because the carrier gas flow and vaporization step tend to reduce the temperature of the heated plate.

One solution has been to increase the size of the vaporizer and the injection rate of hydrogen peroxide into the vaporizer. Another solution is to employ a multiple firing vaporizer, in which different areas of a vaporizer plate are sequentially supplied with the hydrogen peroxide solution Although helpful, the larger vaporizer still suffers from concentration variations and condensation concerns.

Yet another solution is to use multiple vaporizers to feed a single enclosure. The vaporizers may each be controlled independently, to allow for variations in chamber characteristics. However, the use of multiple vaporizers adds to the cost of the system and requires careful monitoring to ensure that each vaporizer is performing efficiently.

The present invention provides a new and improved vaporization system and method which overcomes the above-referenced problems and others.

SUMMARY OF THE INVENTION

In accordance with one aspect of the present invention, a vapor decontamination system for decontaminating a plurality of items is provided. The system includes a flash vaporizer for vaporizing into a vapor a liquid which includes an antimicrobial. A means for introducing the liquid from a source to the flash vaporizer is provided. A first duct along which a carrier gas passes is fluidly connected with at least one fill line which selectively supplies vapor and carrier gas to at least one of the items. A second duct, fluidly connected with an outlet of the vaporizer, supplies the vapor into the first duct for mixing into the carrier gas passing through the first duct.

In accordance with another aspect of the present invention, a method of decontaminating containers in a defined region is provided. The method includes conveying the containers through the defined region and pumping a carrier gas through a duct to the defined region. An antimicrobial vapor is introduced into the duct at a mixing zone upstream of the defined region.

In accordance with another aspect of the present invention, a method of decontaminating items is provided. The method includes conveying the items through a defined region. First and second carrier gas streams are provided, the first stream having a lower flow rate than the second stream. The first stream is introduced to a passage. A flow of an aqueous solution of an antimicrobial is introduced into the passage. The aqueous solution mixes with the first stream. Walls of the passage are heated to vaporize the aqueous solution. The vaporized aqueous solution and first carrier gas stream are mixed with the second carrier gas stream in a mixing zone downstream of the passage. The mixed vaporized aqueous solution and first and second carrier gas streams are introduced to the defined region and the items contacted with the antimicrobial.

One advantage of at least one embodiment of the present invention is that a high output of vaporized hydrogen peroxide is achieved.

Another advantage of at least one embodiment of the present invention is that it enables a large throughput of containers to be decontaminated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1 is a schematic view of one embodiment of a hydrogen peroxide decontamination system in accordance with the present invention;

FIG. 2 is a side sectional view of one embodiment of the vaporizer of FIG. 1;

FIG. 3 is a perspective view of the vaporizer of FIG. 2;

FIG. 4 is a perspective view of a second vaporizer embodiment;

FIG. 5 is a side sectional view of a third vaporizer embodiment;

FIG. 6 is a side sectional view of a fourth vaporizer embodiment;

FIG. 7 is a side sectional view of a fifth vaporizer embodiment;

FIG. 8 is a schematic view of another embodiment of a hydrogen peroxide decontamination system in accordance with the present invention;

FIG. 9 is a side sectional view of a hydrogen peroxide vapor supply with a container cap, according to another embodiment of the present invention;

FIG. 10 is a schematic view of another embodiment of a hydrogen peroxide decontamination system in accordance with the present invention;

FIG. 11 is a schematic view of another embodiment of a hydrogen peroxide decontamination system in accordance with the present invention;

FIG. 12 is a schematic view of another embodiment of a hydrogen peroxide decontamination system in accordance with the present invention; and FIG. 13 is a side sectional view of a blow molding apparatus used for simultaneous hydrogen peroxide vapor decontamination.

DETAILED DESCRIPTION OF THE PREFERRED EMBODIMENTS

With reference to FIG. 1, a system for supplying vapor hydrogen peroxide to an aseptic filling plant A includes a flash vaporizer 10, which converts liquid hydrogen peroxide to vaporized hydrogen peroxide. The vapor produced is then injected into a carrier gas and carried in the gas to a site, such as a decontamination tunnel 11, where the vapor is to be used. Alternatively, the vapor is drawn under a vacuum to the tunnel 11. The vaporizer allows for continuous production of vapor hydrogen peroxide for microbial decontamination of the decontamination tunnel and its contents. While the invention is described with particular reference to hydrogen peroxide, it will be appreciated that the system is also applicable to vaporization of other solutions and pure liquids, such as the formation of peracetic acid vapor from a peracetic acid solution.

The term "microbial decontamination" and similar terms, as used herein, encompass sterilization, disinfection, and lesser forms of antimicrobial treatment, such as sanitization.

With continued reference to FIG. 1, a means for introducing liquid hydrogen peroxide, such as an injection pump 12, such as adjustable metering pump, pressurized container, gravity feed system, or the like, deposits liquid hydrogen peroxide, preferably in the form of a liquid flow or spray, from a cartridge or reservoir 14, such as a large drum, into the vaporizer 10 from a supply line 16.

With reference also to FIG. 2, the vaporizer includes a heated block 18, which may be formed from a metal, such as anodized aluminum, or other material resistant to hydrogen peroxide. A fluid pathway 19 is defined by a series of bores 20, formed in the block. The fluid pathway 19 has an inlet 22, connected with the supply line, and an outlet 24. In one embodiment, the bores 20 progressively increase in internal diameter from the inlet 22 to the outlet 24, thus creating an increasing area of contact and internal volume per unit length. The liquid hydrogen peroxide contacts the wall 26 of the bore and is vaporized. The increasing volume of the vapor/liquid mixture passing through the bore is accommodated by the increasing cross sectional area of the bore.

The liquid hydrogen peroxide includes a mixture of hydrogen peroxide in a diluent, such as water, preferably an aqueous mixture comprising about 30–40% by weight hydrogen peroxide in water, more preferably, about 35% by weight hydrogen peroxide. Optionally, a carrier gas, such as air, nitrogen, carbon dioxide, helium, argon, or a combination of carrier gases, is fed into the flash vaporizer concurrently with the hydrogen peroxide liquid to assist in propelling the peroxide vapor through the flash vaporizer and injecting it into the carrier gas flow. In a preferred embodiment, the carrier gas includes pressurized air from an air reservoir 28, which is introduced to the vaporizer either along with or separately from the liquid hydrogen peroxide, via an inlet line 30 (FIG. 1). The exact pressure of the incoming carrier gas varies with the production rate, the length and restrictiveness of passages in the flash vaporizer, and the like, and typically varies from 1.0–2.0 atmospheres absolute ($1.013\times10^5$–$2.026\times10^5$ Pascals absolute), i.e, about 0–1 atm. gauge (0–$1.013\times10^5$ Pascals gauge), more preferably, about 6–$14\times10^3$ Pa. An advantage of using such a carrier gas centers on the fact that the liquid hydrogen peroxide is unlikely to continuously impinge on the same point in the vaporizer. The more dispersed the liquid hydrogen peroxide is within the vaporizer, the more readily the peroxide will be vaporized. In addition, with a well dispersed hydrogen peroxide injection, the less likely that specific regions of the vaporizer will experience undue cooling thereby hindering the vaporization process.

The carrier gas tends to cool the vaporizer, reducing the rate at which the aqueous hydrogen peroxide solution is vaporized. Consequently, it is desirable to maintain the carrier gas at or slightly above a minimum flow rate needed to carry the vaporized hydrogen peroxide through the flash vaporizer 10 without significant degradation of the peroxide vapor, but at a flow rate which is low enough such that appreciable cooling of the vaporizer by the carrier gas does not occur.

Figure 2:
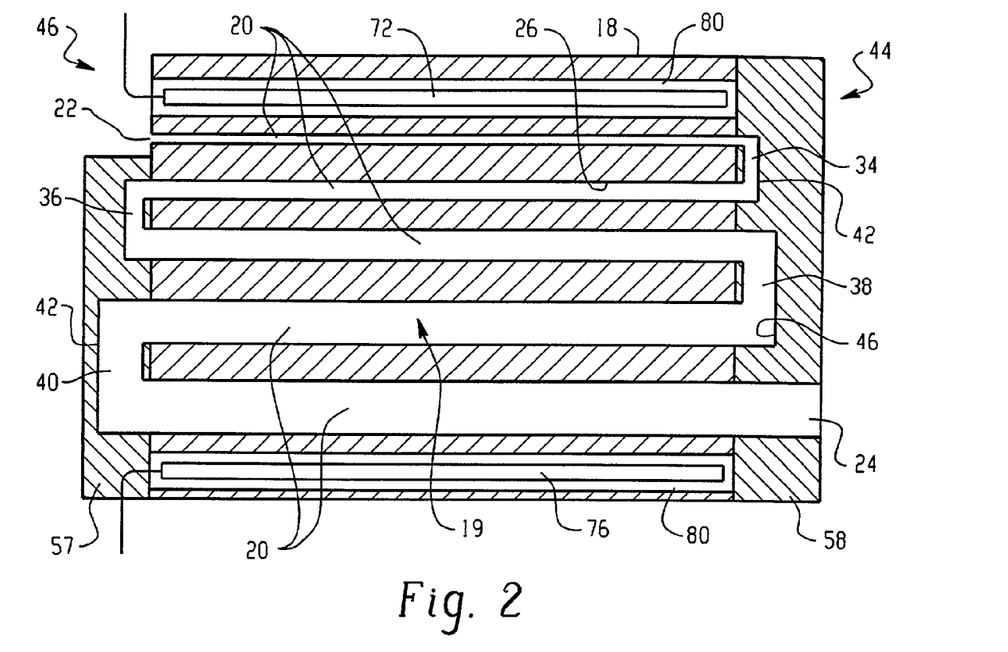
Figure 3:
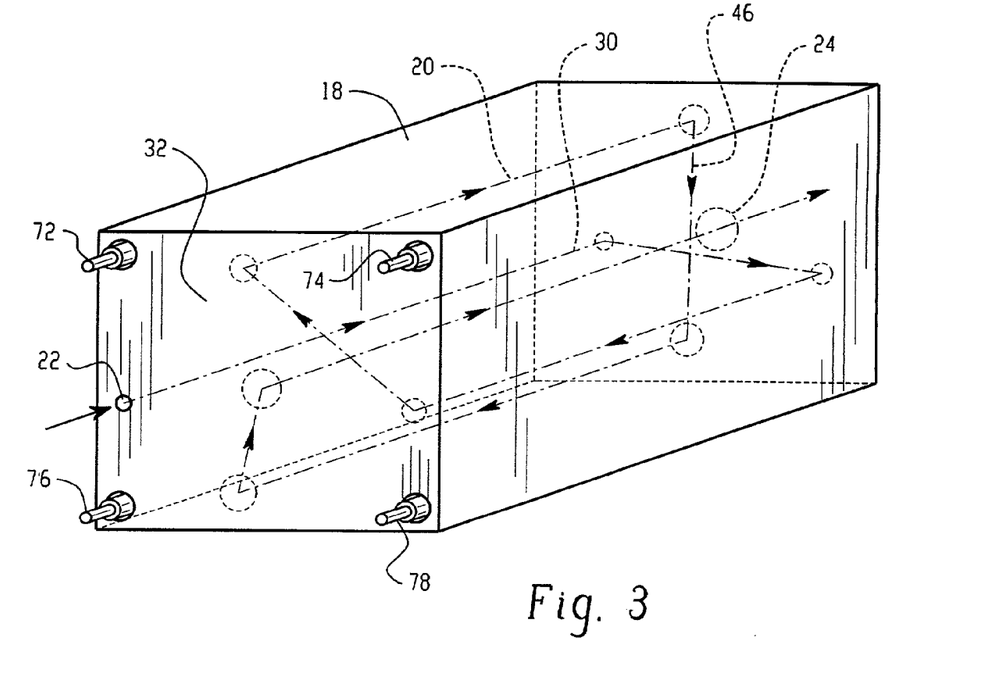

As shown in FIG. 3, the longitudinal bores are joined by connecting members 34, 36, 38, 40, which may be formed within the block, or external thereto, as shown in FIG. 2. Other arrangements are contemplated, such as a spiral bore of increasing cross sectional area, or bores which each increase in cross section from one end of the block to the other. In yet another embodiment, the number of bores increases with each pass through the block. Thus, a single longitudinal bore for the first pass is connected with two, or more bore portions for the second pass. Each of these second bores is also connected with two, or more bores for the third pass, and so forth. In this way, as for the earlier embodiments, the cross sectional area of the fluid pathway 19 created by the bores increases as the hydrogen peroxide travels from the inlet to the outlet (in this case, a plurality of outlets).

The bends or turns 42 in the fluid flowpath 19 cause the liquid hydrogen peroxide to change directions and thereby encourages the liquid to hit the walls and vaporize. Preferably, at least two substantially 180 degree turns are provided in the flowpath to provide this increased contact (four such turns are shown in FIG. 2).

In each of the embodiments, the bore may make several turns within the block. For example, starting at the bore inlet 22, the bore makes a U-turn 42 adjacent an outlet end 44 of the block, returns to an inlet end 46 of the block, and makes two more such turns before reaching the outlet 24. Preferably, the turns are formed by sharp, "L-shaped" rather than rounded turns. For example, as shown in FIG. 2, each turn includes two approximately 90° corners and an end wall 46, which turn the bore through approximately 180°. Having generally sharp, rather than rounded corners encourages the flowing liquid/vapor mixture to hit the walls, thereby improving the rate of vaporization.

Figure 4:
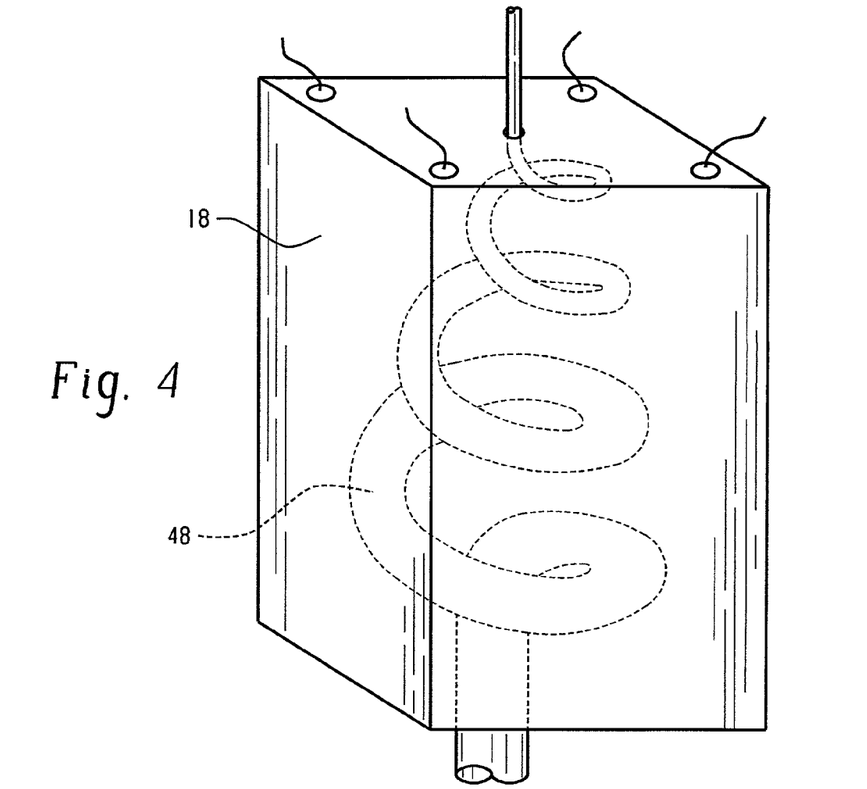

Other arrangements are contemplated, such as a spiral bore 48, as shown in FIG. 4. At each turn, inertia tends to propel fine, suspended droplets into the walls resulting in the vaporization of the droplets. In this manner, any fine droplets of mist or fog are turned to vapor. Preferably, at least two substantially 180° turns are provided in the flowpath to assure this increased contact.

Figure 5:
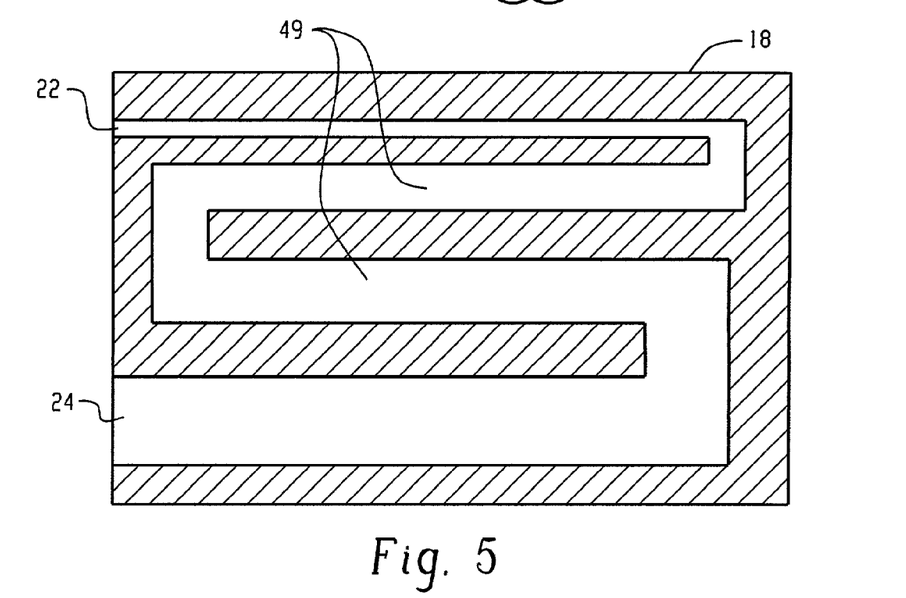

The increasing diameter may be provided by progressively increasing the diameter of each segment of the bore, as shown in FIG. 2. Alternatively, longitudinal portions 49 of the bore can each be of a single, successively larger diameter, as shown in FIG. 5. Other arrangements for progressively increasing the bore diameter are also contemplated. For example, baffles or fins may be provided adjacent the inlet to reduce the available flow space while increasing heated surface area.

Figure 6:
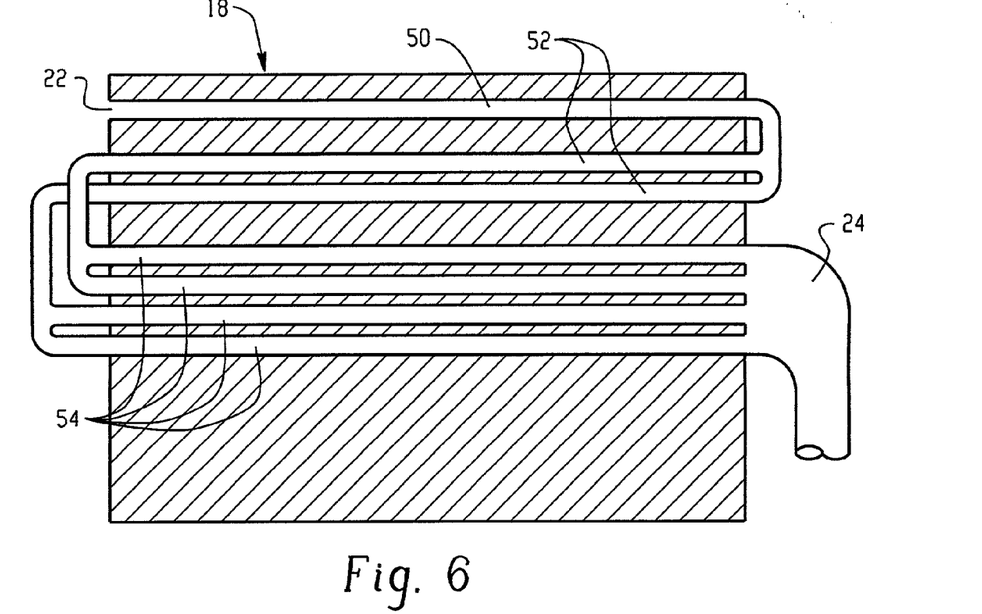

In the embodiment of FIG. 6, the number of bore portions increases with each pass through the block. For example, a single longitudinal bore 50 defines the first pass, two or more bore portions 52 define the second pass. Each of the second bores is preferably connected with more bores 54 for a third pass, and so forth. In this way, as for the earlier embodiments, the cross sectional area of the fluid pathway created by the bores increases as the hydrogen peroxide travels from the inlet to the outlet (in this case, a plurality of outlets).

Figure 7:
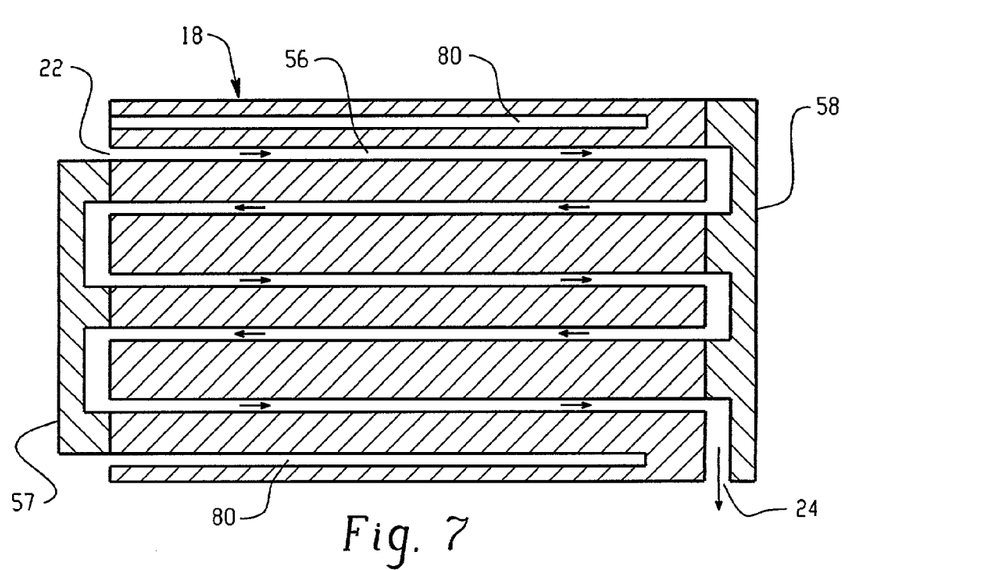

In an alternative embodiment, shown in FIG. 7, a bore 56 comprising one or more bore portions of uniform cross sectional area is provided, such that the entire bore or majority of the bore is of uniform cross sectional area. It is also contemplated that, for ease of manufacture, longitudinal bore portions may extend through the block, for example by drilling right through the block. The lateral portions are defined outside the main body of the block, by molded aluminum end pieces 57, 58 (FIG. 2), connecting tubing, or the like. The end pieces or connecting tubing are maintained at the temperature of the block and may be surrounded with a heating element, such as a heating tape with insulation, or the like.

With reference once more to FIGS. 2 and 3, the block 18 is heated to a suitable temperature for vaporizing the liquid hydrogen peroxide. For example, heating elements 72, 74, 76, 78 are received in bores or passageways 80, preferably drilled longitudinally through the block adjacent the corners of the block. Suitable heating elements are electric cartridge heaters. Such heaters are particularly appropriate for use as the heating element as they are commonly elongated and thin so that each heating element can be inserted into a heater bore and extend substantially from one end of the bore to the other. Alternatively, steam, or other heated fluid, is passed into the heater bores to heat the block. The bore wall is maintained by the heaters at a temperature below that at which dissociation of the hydrogen peroxide occurs.

The liquid hydrogen peroxide vaporizes as it contacts the wall of the bore and is progressively converted from a liquid to a vapor. The increasing pressure which would normally result from this conversion is substantially eliminated by the increase in size of the bore such that the flow through the bore is maintained. At the end of the series of passes through the block, the hydrogen peroxide is preferably entirely in vapor form, at a temperature and pressure which maintain the vapor slightly above the dewpoint temperature, such that condensation of the vapor does not occur.

Figure 1:
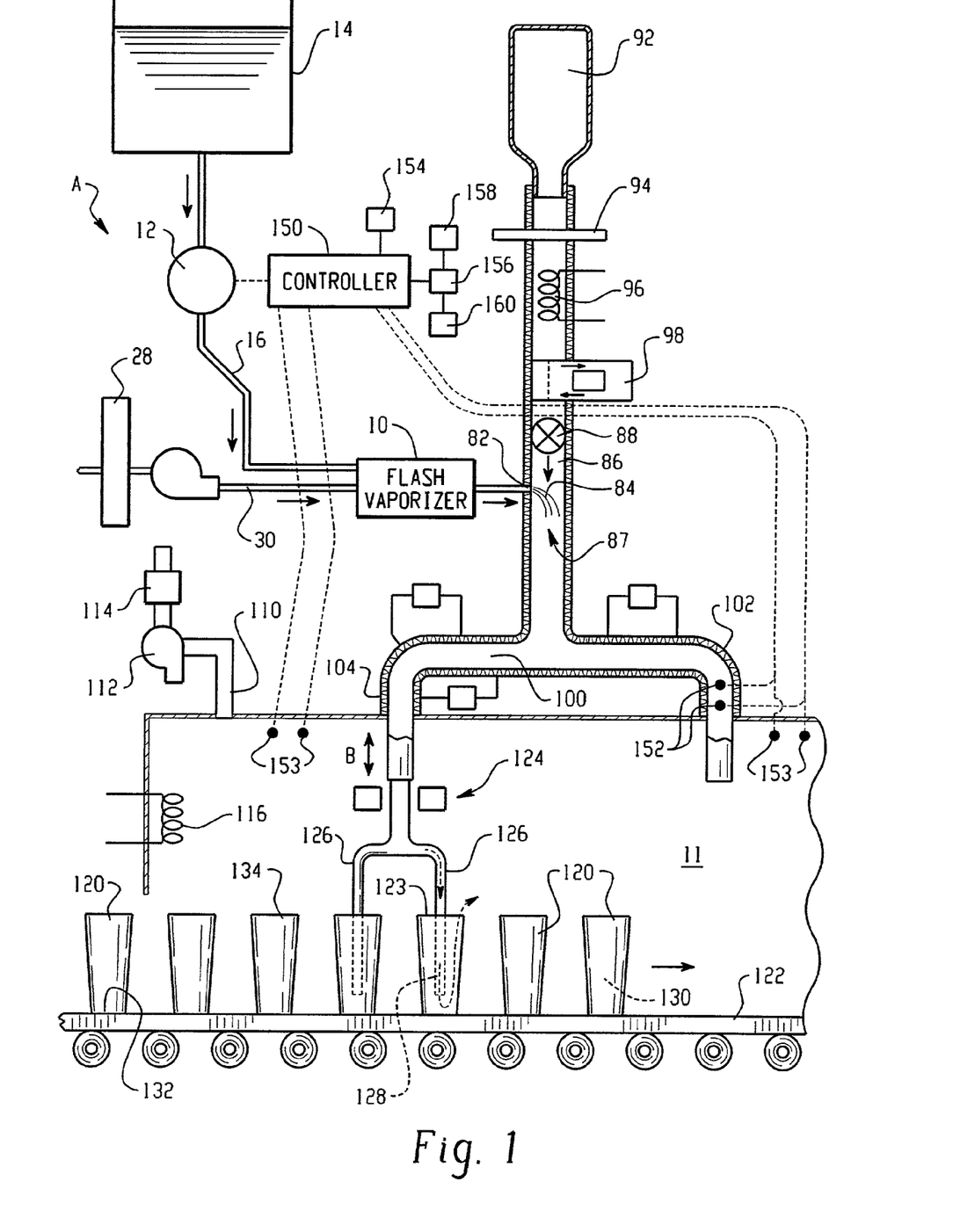

The vapor hydrogen peroxide is then entrained in a flow of a carrier gas. Specifically, as shown in FIG. 1, the vapor (optionally, together with the first stream of carrier gas) travels along a duct or line 82 to a nozzle or nozzles 84, or other suitable injection device, which injects the vapor into a carrier gas duct or line 86 in a mixing zone 87. The vapor is entrained, at the mixing zone, in a stream of air or other carrier gas flowing through the line 86. A carrier gas flow regulator or baffle 88 adjustably controls the flow of carrier gas. Adjusting the metering pump 12 controls the rate at which the hydrogen peroxide vapor is produced and adjusting the carrier gas flow regulator 88 controls the concentration in the carrier gas. The air and vapor mixture is carried to the tunnel 11 in which the vapor is to be used, in this case a chamber of the aseptic filling system. Optionally two or more vaporizers 10 may feed into a single carrier gas line 86. For large decontamination tunnels, several, independently controllable vaporizers 10, each with an air line 86, may feed into the decontamination tunnel 11.

The carrier gas is preferably air, although other gases which are unreactive toward hydrogen peroxide, as discussed above, are also contemplated. A carrier gas source 92, such as a pump or container of pressurized gas, supplies the carrier gas to the line 86. When atmospheric air is the carrier gas, a filter 94, such as an HEPA filter, remove contaminants. Preferably, a preheater 96 raises the temperature of the carrier gas before it reaches the injectors 84, reducing condensation in the supply lines and raising the saturation concentration of hydrogen peroxide vapor. Optionally, a dryer 98 or the like controls the humidity of the carrier gas.

The flow rate of carrier gas through flash vaporizer 10 (i.e., that of the first carrier gas stream) is preferably lower than the flow rate of the second carrier gas stream which does not pass through flash vaporizer 10. The majority of the carrier gas thus travels through line 86 from the source 92 to the mixing zone 87 downstream of the vaporizer, where both the first and second carrier gas streams and the vapor are combined prior to entering the enclosure. The flow rate of the first stream is preferably less than 10% of the flow rate of the second stream. For example, the combined carrier gas streams may have a flow rate of about 20,000 liters/minute, while the carrier gas stream flowing through the flash vaporizer is 100 liters/min or less, more preferably, about 20 liters/min or less, most preferably, about 1–10 liters/min. Where there is no first carrier gas stream used, all of the carrier gas preferably passes through the carrier gas line 86.

While the flash vaporizer 10 thus described is suited to high throughput applications, such as this, other vaporizers are also contemplated. For example, a drip vaporizer or multiple vaporizers may be used. In such a vaporizer, a flow of carrier gas passes over a heated plate. Liquid hydrogen peroxide is dripped on to the plate and is vaporized. The vapor is entrained in the passing air and is carried in the air to the decontamination tunnel 11. As in the prior embodiment, the air, or other carrier gas, may be heated to a suitable temperature. The air is preferably dried before passing through the vaporizer to increase the concentration of hydrogen peroxide which can be sustained at a given temperature.

Supply lines 100, 102 transport the mixture of carrier gas and vaporized hydrogen peroxide to the tunnel 11. To reduce the risk of condensation, the length of the supply lines 100, 102 is minimized. To reduce the risk of condensation further, insulation 104 and/or heaters 106 surround the supply lines 100, 102. Optionally, two or more supply lines connect each vaporizer to two or more regions of the tunnel 11.

A vent 110 permits controlled release of vapor from the decontamination tunnel. A pump, such as a vacuum pump 112 applies suction to the tunnel to draw used (i.e, partially spent) vapor from the tunnel. Alternatively, blowers are used. Optionally, destroyer, such as a catalyst 114 or the like breaks down any residual hydrogen peroxide in the vented gas. The carrier gas may be recycles to the carrier gas line 86.

Optionally, a heater 116 maintains the temperature of the tunnel 11 during microbial decontamination. Raising the temperature in the decontamination tunnel above ambient temperature or at least its surfaces also reduces vapor condensation.

Figure 8:
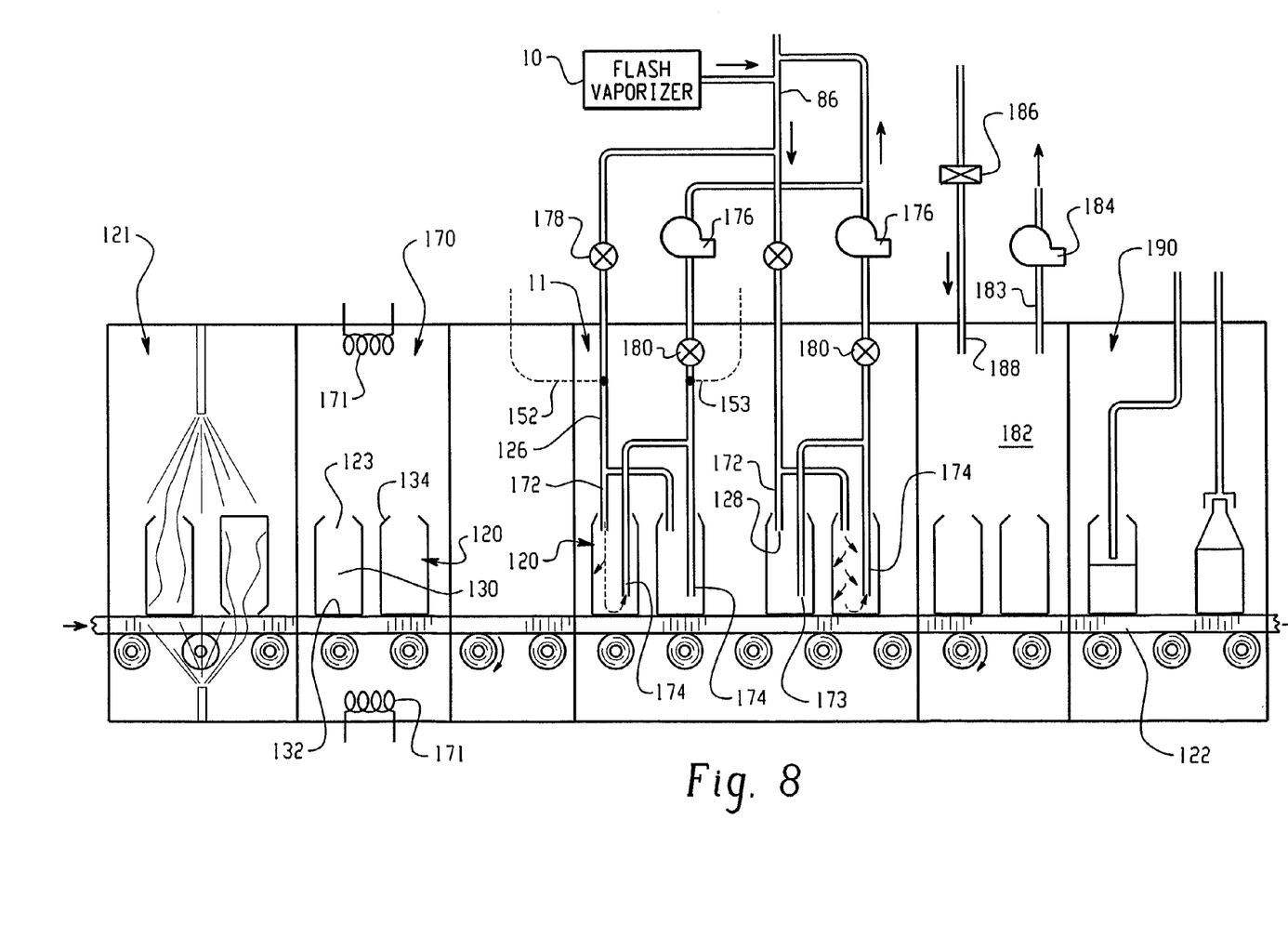

With reference to FIGS. 1 and 8, containers, such as bottles or cartons 120, for example, plastic beverage containers and wax-coated milk and juice cartons are carried into the decontamination tunnel on a conveyor system 122, such as an indexing conveyor belt. Each of the containers has an opening 123, through which the vapor is introduced. A reciprocating manifold 124 is connected with the each of the supply lines 100, 102 and sequentially raises and lowers (in the direction of arrows B) a number of fill lines 126 into the bottles or cartons as they pass by. The hydrogen peroxide thus flows directly from a discharge outlet 128 of the fill line into an interior space 130 of the container. Alternatively, the manifolds are kept stationary and the containers are lifted as they pass by to receive the hydrogen peroxide vapor.

The hydrogen peroxide concentration in the solution is selected according to the desired vapor concentration. For example, the hydrogen peroxide concentration may be from 25–65% by weight aqueous hydrogen peroxide. In one embodiment, the hydrogen peroxide concentration is from about 30–35% by weight aqueous hydrogen peroxide. At this level, condensation of hydrogen peroxide is limited, while microbial decontamination is achieved in a short period of time.

In this embodiment, the fill line is preferably positioned near a bottom end 132 of the container, such that the vapor contacts all interior surfaces of the container before it is drawn out of the opening 123 at or adjacent the top 134 of the container by the vacuum 112. The hydrogen peroxide vapor is held in each of the containers until microbial decontamination is complete. The vacuum pump 112 draws out the hydrogen peroxide vapor from the decontamination tunnel, creating a suction on the containers which pulls the vapor out of the containers following microbial decontamination. This reduces the time required for dissipation of the hydrogen peroxide.

In the illustrated embodiment, the vaporizer 10 is preferably located in close proximity to the decontamination tunnel. Where more than one vaporizer is used, the rate of introduction of hydrogen peroxide by the individual vaporizers is adjustable so as to optimize hydrogen peroxide vapor distribution within the decontamination tunnel 11.

Differences in temperature and absorbency of materials within the decontamination tunnel 11, flow patterns in the tunnel, and tunnel shape are among the factors influencing the optimum rate of introduction. The rate of throughput of containers or bottles through the tunnel also influences the optimum rate of introduction. Preferably, a control system 150 regulates the introduction of hydrogen peroxide to the vaporizer(s) 10 in accordance with detected conditions within the decontamination tunnel 11. A plurality of monitors 152, 153 monitor conditions within the tunnel. The monitors include, for example, one or more temperature sensors, one or more dewpoint or humidity sensors, one or more vapor concentration sensors, one or more air flow or turbulence sensors, one or more pressure sensors, and the like. The control system includes a comparator 154 for comparing the monitored condition signals from the monitors with preselected ideal hydrogen peroxide vapor concentration and other conditions as indicated by reference signals. Preferably, the comparator determines a deviation of each monitored condition signal from the corresponding reference signal or a reference value. Preferably, a plurality of the conditions are sensed and multiple comparators are provided. A processor 156 addresses a pre-programmed look up table 158 with each deviation signal (or combination of deviations of different conditions) to retrieve a corresponding adjustment for each vaporizer 10. Other circuits for converting larger deviations to larger adjustments and smaller deviations to smaller adjustments are also contemplated. Alternately, the error calculation can be made at very short intervals with constant magnitude increases or decreases when the monitored condition is below or above the reference points.

The adjustment values from the look up table adjust the hydrogen peroxide metering pump 12 and the carrier gas regulator 88 to bring the monitored conditions to the reference values. For example, vapor injection rates are increased by vaporizers near regions with lower vapor concentration, lower temperatures, higher pressure, and the like. Vapor production rates are reduced in response to higher sensed vapor concentration, higher sensed temperatures, lower pressure, and the like. The processor, optionally, also controls the tunnel heater 116, circulation fans in the decontamination tunnel, the vacuum pump 112, or the like to maintain the preselected tunnel conditions. Optionally, an operator input 160 enables the operator to adjust the reference signal in each region to cause higher or lower concentrations in selected regions.

For example the dewpoint of the vapor may be measured with sensors 152 positioned at the point of delivery and also sensors 153 in or adjacent to the exit line 110. The two measurements are used to allow feedback control and to ensure that the containers have been sufficiently exposed to the vapor hydrogen peroxide under conditions sufficient to provide sterility. The temperature of individual containers may also be measured if the process does not control the temperature of the incoming containers with sufficient accuracy. This information can be fed to the control system. The control system causes the vaporizer to modify the dewpoint of the vapor produced to ensure that condensation does not occur. Alternatively or additionally, the residence time of the containers in the decontamination zone is modified, for example, by reducing the speed of the conveyor system, to provide the desired level of microbial decontamination. Monitoring the vappor hydrogen peroxide exhaust line provides a worst case/lowest concentration area in the system. Continuously refreshing the vapor in the tunnel while withdrawing the spent vapor provides greater process control and allows the prevention of higher background water vapor levels building up over time as the peroxide degrades.

The vaporizer 10 is capable of achieving a higher vapor output than conventional, drip-type vaporizers. For example, a heating block which supplies 1653 watts to the bores is able to vaporize 50 grams of hydrogen peroxide/minute (35% hydrogen peroxide, 65% water), since the heat of vaporization of the solution is 33.07 watt-min/gram. Obviously, as the heat supplied increases, correspondingly higher outputs can be achieved. Using one or more of such vaporizers, a high speed bottling line (e.g., about 1000 bottles/min) can be decontaminated.

The present inventors have found that any condensation of the vapor hydrogen peroxide on the containers makes it very difficult to achieve the low levels of hydrogen peroxide residuals on food containers currently mandated. To reduce the level of hydrogen peroxide residuals on the decontaminated containers, it is desirable to ensure that condensation of the hydrogen peroxide vapor on the containers is eliminated or kept to a minimum. To achieve this, conditions within the decontamination tunnel 11 and around the bottles are carefully monitored and controlled to keep the vapor slightly above its dewpoint temperature, to maximize the rate of decontamination while reducing the risk of condensation. The dewpoint temperature is preferably maintained at over 90% of the temperature of the chamber, more preferably, at between about 90 and 95% of the dewpoint temperature. With better control algorithms, the dewpoint temperature may be between 95% and 100% of the chamber temperature.

Additionally, especially when the decontamination tunnel is heated to above ambient temperature, the containers are preferably preheated prior to admitting the vapor. With reference to FIG. 8, the containers pass through a heating chamber 170 prior to entering the decontamination tunnel 11, where the containers are heated by heaters 171 to a sufficient temperature such that the surfaces of the containers are at or above the temperature of the tunnel when the containers enter the tunnel. This avoids condensation occurring on the containers.

With continued reference to FIG. 8, a circulating flowpath may be created in each of the containers by supplying the vapor hydrogen peroxide through a fill line 172 to one end of the container (near the top 134 in FIG. 8) and withdrawing the vapor through an inlet 173 of an exhaust line 174 positioned near the other end of the container (the base 132 in FIG. 8) using a pump 176. In this way, the vapor is drawn through the container and rapidly contacts the entire surface. Within about 1–2 minutes, the interior of the container is microbially decontaminated to at least a high level disinfection standard. Optionally, the tubes may be operated sequentially, with a first valve 178 being opened for a brief period to allow a pulse of hydrogen peroxide to enter the container through the fill line 172. The fill line valve 178 is then closed. After a brief decontamination period, perhaps 30 seconds to one minute, depending on the temperature, a second valve 180 is opened and the pump 176 withdraws the vapor from the container through the exhaust line 174.

Further removal of hydrogen peroxide from the containers may take place in an aeration chamber 182, connected with the decontamination tunnel 11, which is subjected to a negative pressure via an exhaust line 183 connected with a vacuum pump 184. Or, the exhaust lines in the decontamination chamber may be eliminated and the containers continue to be decontaminated as they pass into the aeration chamber. The vapor is then removed in the aeration chamber.

Alternatively or additionally, sterile air, which has been passed though a filter 186 is blown into the aeration chamber through an air inlet line 188 to drive any remaining vapor from the containers. Pressure differences and/or air flow through filters, such as HEPA filters in the interface areas between the decontamination tunnel and the aeration chamber may be used to minimize the risk of cross-contamination. The decontaminated containers then move to an aseptic filling area 190 where they are filled with the product and then capped.

The length of the decontamination tunnel, the speed of the conveyor system, temperature of the tunnel, and the chemistry of the vapor are selected so as to ensure that the containers are microbially decontaminated by the time the vapor is removed. In a preferred high speed bottling plant, each container spends about one to two minutes in the decontamination tunnel, during which time it is microbially decontaminated.

Figure 9:
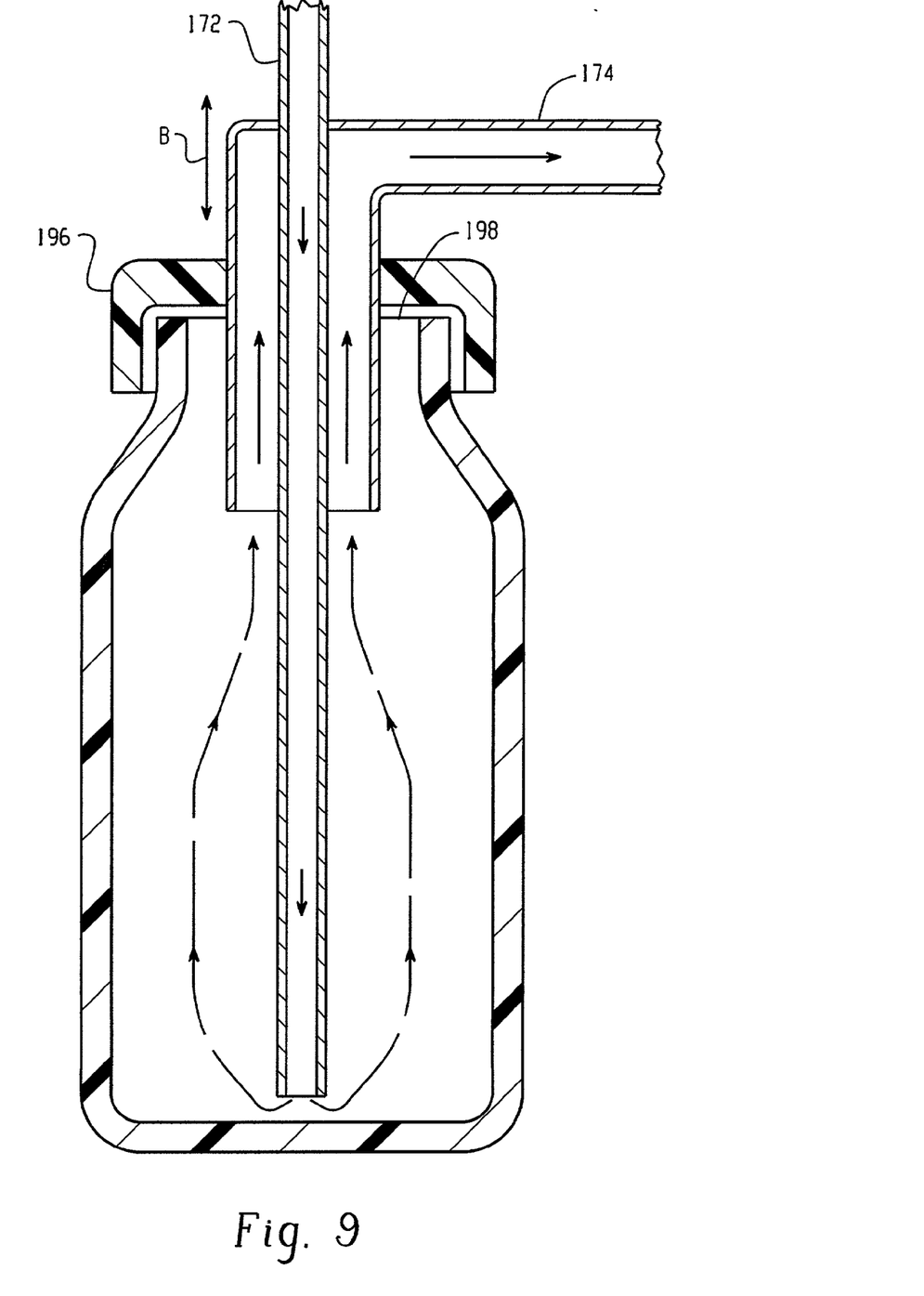

The fill and exhaust lines 172, 174 may be in the form of side by side tubes, as shown in FIG. 8, or may be concentric tubes, as shown in FIG. 9. The lengths of the fill and exhaust lines can, of course be reversed, so that the vapor enters near the top of the container and is withdrawn from adjacent the bottom.

Figure 10:
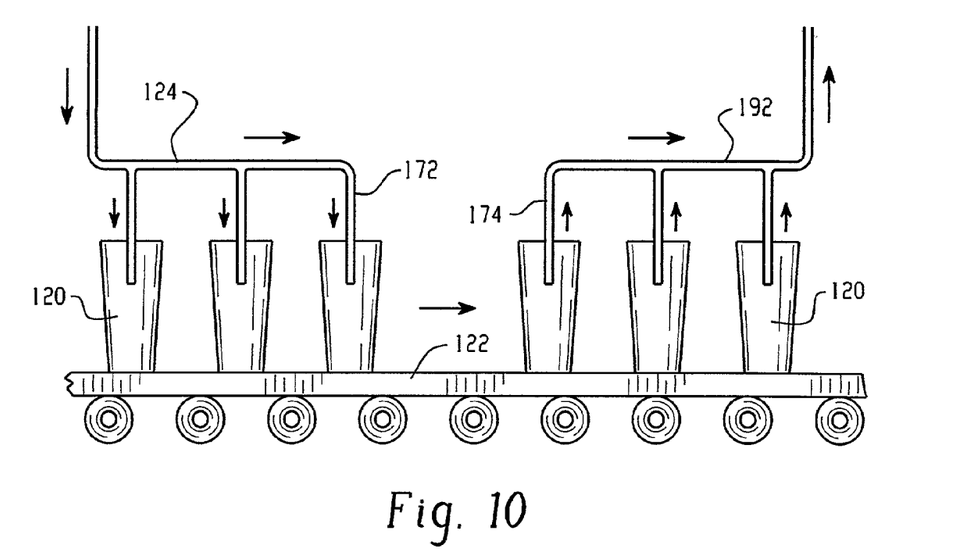

Alternatively, as shown in FIG. 10, the fill and exhaust lines may be separately introduced to the containers. First, a set of containers is filled with vapor from an inlet manifold 124 connected to a set of fill lines 172. The containers then pass to a second, exhaust manifold 192 connected to a set of exhaust lines 174. The spacing between the two manifolds is arranged to allow sufficient residence time for the vapor to decontaminate the containers before the containers reach the exhaust manifold.

With reference once more to FIG. 9, a cap 196 optionally at least partly closes off a top opening 198 of the container during vapor introduction and removal. As shown in FIG. 9, the cap has apertures formed therein through which the fill and exhaust lines 172, 174 pass.

Figure 11:
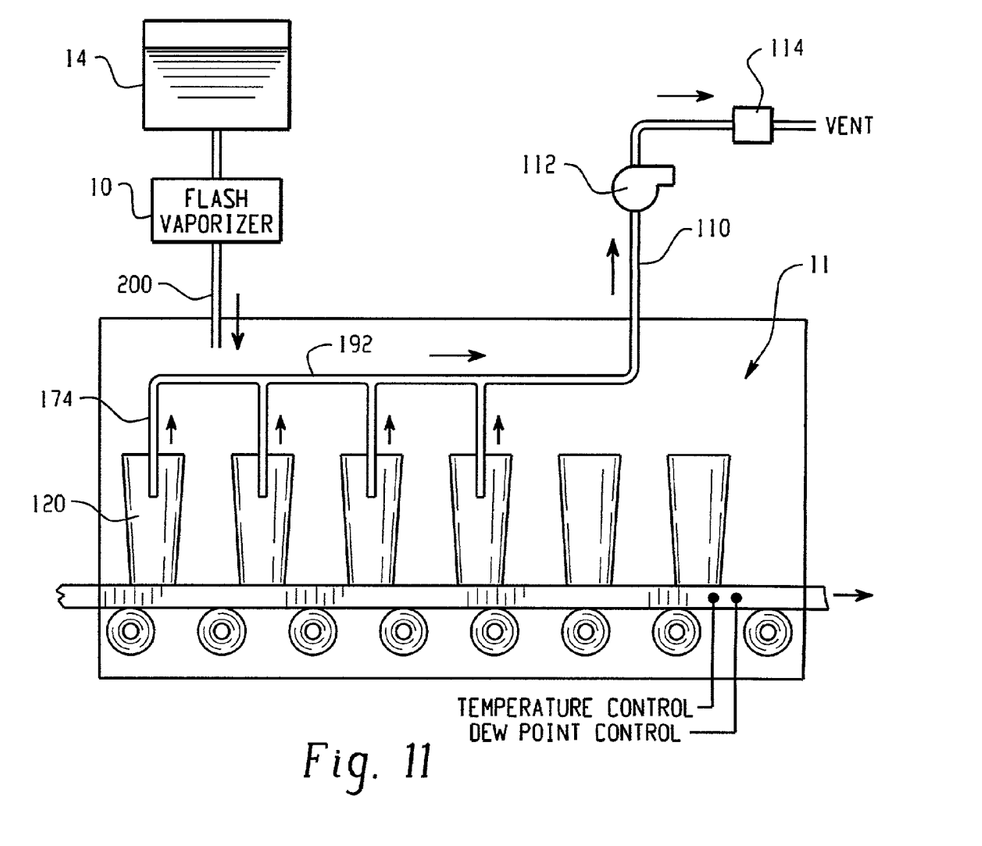

In another embodiment shown in FIG. 11, the hydrogen peroxide vapor is fed into the decontamination tunnel through an inlet line or fill line 200 and is drawn into the individual containers by applying a vacuum to exhaust lines 174 inserted into each container. The exhaust lines extend to near the bottom of each container so that the vapor is drawn through the container to achieve decontamination.

Figure 12:
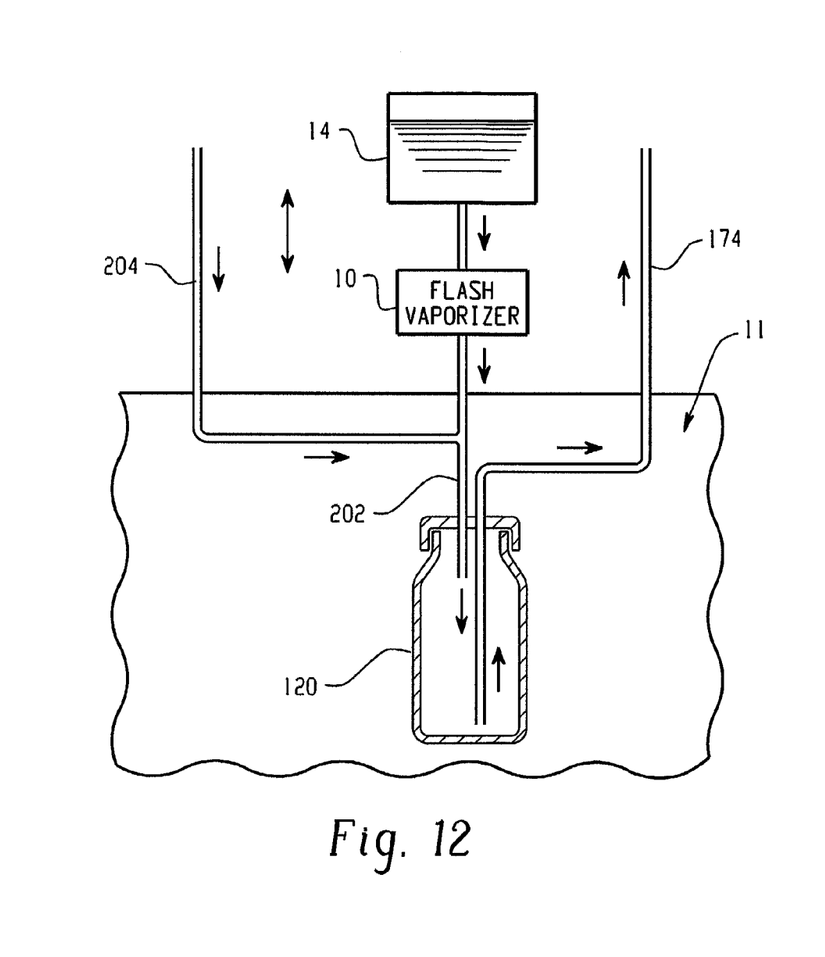

In another embodiment, shown in FIG. 12, each fill line 202 has its own dedicated vaporizer 10, which may be located very close to the containers, e.g., in the decontamination tunnel 11. An exhaust line withdraws the vapor from the containers. A carrier gas line 204 may be used to supply a carrier gas to the inlet line or the vapor may be passed directly to the container without use of a carrier gas.

The containers preferably pass though a reduced pressure enclosure 206 prior to entering the decontamination tunnel to limit escape of the vapor into other areas of the bottling line.

Figure 13:
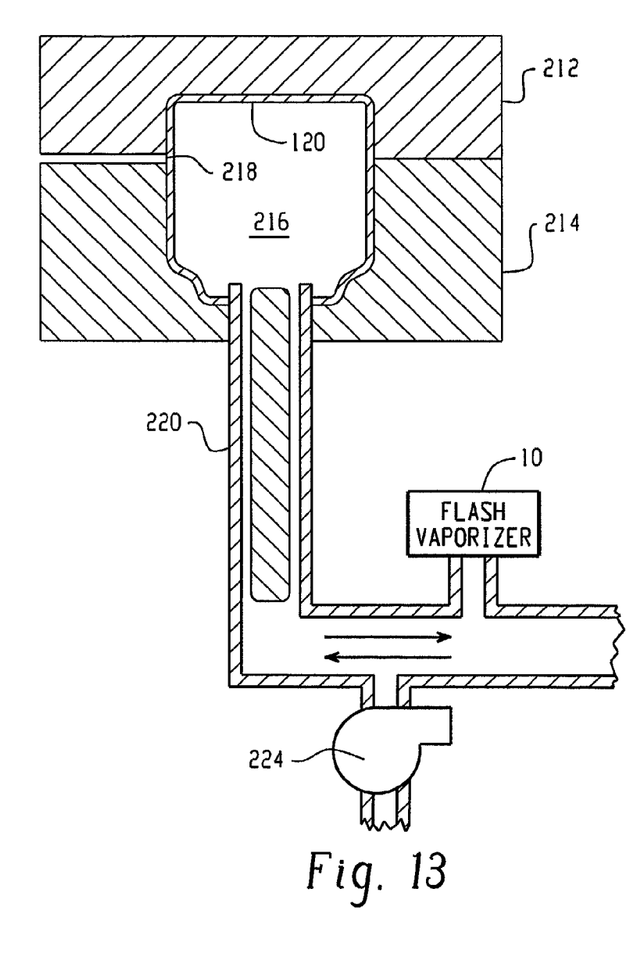

In another embodiment, shown in FIG. 13, vapor hydrogen peroxide is introduced to containers during the blow molding process. In bottling plants which blow mold containers shortly before filling with the product, the containers can be microbially decontaminated and remain contaminant free until filling. For example, the vapor hydrogen peroxide is introduced with or in place of the gas traditionally injected into a partially set parison during blow molding. The vapor hydrogen peroxide is removed along with the injection gas once the parison has fully set.

The blow mold includes two mold halves 212, 214 which define an interior chamber 216. Molten thermoplastic material is introduced to the chamber via an inlet 218. Fluid, conventionally a gas, is then introduced under pressure to the chamber through an injection needle 220. The fluid pushes the setting parison against the walls of the chamber where it sets into the shape of the chamber. The vapor hydrogen peroxide can be introduced in place of or combined with a conventional fluid. The heat of the still warm parison helps to maintain the hydrogen peroxide in the vapor state. Or, the hydrogen peroxide vapor may be introduced to the chamber later, through the same injection needle, once the parison has almost or completely set. The fluid used to shape the parison may be withdrawn or partially withdrawn prior to admitting the vapor. Once decontamination has been achieved, the vapor is then withdrawn via the injection needle using a pump 224.

Table 1 provides exemplary process conditions for achieving rapid antimicrobial decontamination.

TABLE 1

| Process Temperature (° C.) | VHP Concentration (Mg/L) at 100% saturation | Estimated D-value (mins) | Time for decontamination (mins) |
|---|---|---|---|
| 4 | 0.3/0.5 | 8–12 | 24–36 |
| 25 | 1–2 | 1–2 | 3–6 |
| 37 | 3–4 | 0.5–1 | 1.5–3 |
| 55 | 10–12 | 0.02 | 0.06 |

The D-values in Table 1 were determined for *Bacillus stearothermophilus* spores. The time for decontamination was based on a 3 log reduction. Since food containers to be decontaminated are generally already at a relatively low level of microbial contamination, a 3 log reduction is expected to be sufficient to achieve sterilization or high level disinfection standards.

The values above were determined for 100% saturation. It is to be appreciated that 100% saturation cannot be achieved in practice without some risk of condensation. Accordingly, if the vapor is maintained at, for example, 90–95% saturation, the time for decontamination will be correspondingly longer than the times given above. The dewpoint of the hydrogen peroxide is preferably maintained just below the operating temperature, i.e., as close as the operating plant is able to achieve without appreciable risk of condensation. For example, if the plant control system is capable of maintaining temperatures to within about 2° C., the operating temperature can be as little as about 3° C. higher than the dewpoint temperature.

As seen from Table 1, the rate at which hydrogen peroxide inactivates microorganisms increases with temperature and with the concentration of hydrogen peroxide. The maximum sustainable hydrogen peroxide concentration is increased as the temperature is increased. Higher temperatures, in addition to achieving faster decontamination rates, have also been found to result in lower levels of residuals on the decontaminated containers. However, as the temperature is increased, the rate of hydrogen peroxide decomposition is also increased. By balancing these variables to obtain the minimum processing time and vapor exposure, optimal performance can be achieved. By controlling the dewpoint/concentration of the hydrogen peroxide vapor, and by preventing condensation of liquid hydrogen peroxide vapor, the residual levels on the container are minimized, allowing a conventional rinse step to be replaced by an aeration step. This minimizes the risk of recontamination of the containers.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A vapor decontamination system for decontaminating a plurality of items, the system comprising:
    a flash vaporizer for vaporizing into a vapor a liquid which includes an antimicrobial;
    a means for introducing the liquid from a source to the flash vaporizer;
    a first duct which bypasses the vaporizer, along which a carrier gas passes, the first duct being fluidly connected with at least one fill line which selectively supplies vapor and carrier gas to at least one of the items;
    a heater which heats the carrier gas passing along the first duct; and
    a second duct, fluidly connected with an outlet of the vaporizer, for supplying the vapor into the first duct for mixing into the heated carrier gas passing through the first duct.

2. The system of claim 1, wherein the items include containers defining an interior space and a discharge outlet of the at least one fill line is selectively positionable such that the interior space of each of the items receives the vapor.

3. The system of claim 2, wherein the discharge outlet of the at least one fill line is selectively positionable in the interior space of each of the items.

4. The system of claim 2, further including a means for withdrawing the vapor from the container interior space.

5. The system of claim 4, further including:
    an enclosure which receives the items; and the means for withdrawing includes a vacuum pump which draws a vacuum on the enclosure, such that vapor is drawn from the container interior space.

6. The system of claim 4, wherein the means for withdrawing includes:
    an exhaust line having an inlet which is selectively receivable in the interior space; and
    a vacuum pump for applying a vacuum to the exhaust line to withdraw the vapor from the interior space.

7. The system of claim 6, further including:
    a means for selectively fluidly connecting the vacuum pump with the exhaust line, whereby the vapor is allowed to remain in the interior space for a period of time sufficient to effect microbial decontamination before withdrawal.

8. The system of claim 3, further including:
a cap associated with the fill line which selectively closes an opening to the interior space of the item during supply of vapor and carrier gas to the interior space.

9. The system of claim 8, wherein the cap receives the fill line and an exhaust line therethrough.

10. The system of claim 1, further including a conveyor system which conveys the items past the at least one fill line.

11. The system of claim 10, further including a reciprocating manifold which sequentially raises and lowers the at least one fill line as the items pass by.

12. A vapor decontamination system for decontaminating a plurality of items, the system comprising:
a flash vaporizer for thermally vaporizing into a vapor a liquid which includes an antimicrobial;
a means for introducing the liquid from a source to the flash vaporizer;
a first duct along which a carrier gas passes, the first duct being fluidly connected with at least one fill line which selectively supplies vapor and carrier gas to at least one of the items, the discharge outlet of the at least one fill line being selectively positionable in the interior space of each of the items, a cap associated with the fill line which selectively closes an opening to the interior space of the item during supply of vapor and carrier gas to the interior space;
a second duct, fluidly connected between an outlet of the vaporizer and the first duct, for supplying the vapor into the first duct for mixing into the carrier gas passing through the first duct; and
a vapor withdrawal system, the vapor withdrawal system including at least one exhaust line associated with the cap which is selectively positioned within the at least one item together with the at least one fill line, whereby vapor is withdrawn from the item.

13. A vapor decontamination system for decontaminating a plurality of items, the system comprising:
a vaporizer for thermally vaporizing into a vapor a liquid which includes an antimicrobial compound which includes hydrogen peroxide, the vaporizer including:
a metal block;
at least one heater for heating and maintaining the metal block at or above a vaporization temperature of hydrogen peroxide and below a hydrogen peroxide disassociation temperature;
a passage extending through the block from an inlet to the outlet, the passage turning at least 180° between the inlet and the outlet;
a means for introducing the liquid from a source to the flash vaporizer adjacent the inlet;
a means for providing a secondary carrier gas flow to the flash vaporizer inlet such that vapor and carrier gas flow from the vaporizer outlet; and,
a main duct along which a main carrier gas flow passes, the vaporizer outlet being fluidly connected with the main duct for delivering the vapor and secondary carrier gas flow into the main carrier gas flow such that the vapor is intermixed with the main carrier gas flow, the main carrier gas flow being larger than the secondary carrier gas flow.

14. The system of claim 13, wherein the passage expands in cross section between the inlet and the outlet.

15. The system of claim 13, wherein the passage includes at least two turns of approximately 90° and a wall therebetween, such that the liquid in the passage strikes the wall, thereby increasing a vaporization rate of the liquid antimicrobial compound.

16. The system of claim 13, wherein the passage includes:
a plurality of interconnected bores extending back and forth through the block between the inlet and the outlet.

17. The system of claim 1, further including:
a dehumidifier connected with the first duct upstream from the second duct.

18. A vapor decontamination system for decontaminating a plurality of items, the system comprising:
a flash vaporizer for thermally vaporizing into a vapor a liquid which includes an antimicrobial, the flash vaporizer including an inlet and an outlet;
a first source of carrier gas connected with the flash vaporizer inlet for supplying a first stream of carrier gas to the vaporizer;
a second source of a carrier gas which supplies a pressurized carrier gas;
a first duct along which a pressurized second stream of carrier gas passes from the second source, the system being configured such that a flow rate of the first stream of carrier gas is less than 10% of a flow rate of the second stream of carrier gas, the first duct being fluidly connected with at least one fill line which selectively supplies vapor and carrier gas to at least one of the items; and
a second duct, fluidly connected between the vaporizer outlet and the first duct, for introducing the vapor and first carrier gas stream into the first duct, mixing the vapor into the second carrier gas stream passing through the first duct.

19. The system of claim 1, further including:
a plurality of fill lines;
at least one additional flash vaporizer and means for introducing liquid fluidly connected with at least one of the plurality of fill lines.

20. The system of claim 1, further including:
a monitor for monitoring concentration of the antimicrobial in an environment around the item; and
a controller connected to the monitor for controlling the means for introducing liquid in accordance with monitored conditions.

21. The system of claim 1, wherein the means for introducing includes a metering pump.

22. A method of decontaminating items comprising:
conveying the items through a defined region;
providing a first carrier gas stream and a pressurized second carrier gas stream, the first stream having a flow rate which is less than 10% of a flow rate of the second stream;
introducing the first stream to a passage;
introducing a flow of an aqueous solution of an antimicrobial into the passage, the aqueous solution mixing with the first stream, walls of the passage being heated to vaporize the aqueous solution;
heating the second carrier gas stream in a duct which bypasses the passage;
mixing the vaporized aqueous solution and first carrier gas stream with the heated second carrier gas stream in a mixing zone downstream of the passage;
introducing the mixed vaporized aqueous solution and first and second carrier gas streams to the defined region; and
contacting the items with the antimicrobial.

23. The system of claim 1, further comprising an injection device connected with the second duct, which injects the vapor from the second duct into the carrier gas in the first duct.

24. The system of claim 23, further comprising a carrier gas source connected with the first duct upstream of the injection device, which supplies carrier gas to the second duct.

25. The system of claim 1, further comprising a carrier gas source connected with the first duct for supplying carrier gas to the first duct which mixes with the vapor entering from the second duct.

26. The system of claim 1, further comprising a duct connected with an inlet with the vaporizer for supplying carrier gas to the vaporizer.

27. A vapor decontamination system for decontaminating containers, the system comprising:
  a vaporizer for vaporizing into a vapor a liquid which includes an antimicrobial;
  a means for introducing the liquid from a source to the vaporizer;
  a conveyor system which conveys containers into a tunnel;
  a first duct which bypasses the vaporizer, along which a pressurized carrier gas passes, the first duct being fluidly connected with at least one fill line which selectively supplies vapor and carrier gas to the containers, a discharge outlet of the at least one fill line being selectively positionable such that an interior space of each of the containers receives the vapor;
  a heater which heats the carrier gas passing along the first duct; and a second duct, fluidly connected with an outlet of the vaporizer, for supplying the vapor into the first duct for mixing into the heated pressurized carrier gas passing through the first duct.

28. The system of claim 27, wherein the system is configured such that the in the first duct gas flow rate is less than 10% of gas flow rate in the second duct.

29. The system of claim 1, wherein the system is configured such that the gas flow rate in the first duct is less than 10% of the gas flow rate in the second duct.

30. The method of claim 22, further including:
  drying the second carrier gas stream; and
  wherein the mixing includes mixing the vaporized aqueous solution and first carrier gas stream with the dried second carrier gas stream.

* * * * *